(12) United States Patent
Leung et al.

(10) Patent No.: US 8,926,675 B2
(45) Date of Patent: Jan. 6, 2015

(54) CONTOURED BONE PLATE

(75) Inventors: Ross T. Leung, Piscataway, NJ (US); Jordan N. Milford, Bethlehem, PA (US)

(73) Assignee: Biomet Manufacturing, LLC, Warsaw, IN (US)

( * ) Notice: Subject to any disclaimer, the term of this patent is extended or adjusted under 35 U.S.C. 154(b) by 1607 days.

(21) Appl. No.: 11/627,018

(22) Filed: Jan. 25, 2007

(65) Prior Publication Data

US 2007/0270853 A1 Nov. 22, 2007

Related U.S. Application Data

(60) Provisional application No. 60/791,228, filed on Apr. 11, 2006.

(51) Int. Cl.
*A61B 17/80* (2006.01)
*A61B 17/84* (2006.01)
*A61F 2/46* (2006.01)

(52) U.S. Cl.
CPC ............. *A61B 17/80* (2013.01); *A61B 17/8057* (2013.01); *A61B 17/842* (2013.01); *A61F 2/4601* (2013.01)
USPC ........................................ 606/291

(58) Field of Classification Search
USPC ..................... 606/280–299, 70–71
See application file for complete search history.

(56) References Cited

U.S. PATENT DOCUMENTS

| | | | |
|---|---|---|---|
| 3,463,148 A | 8/1969 | Treace | |
| 3,716,050 A | 2/1973 | Johnston | |
| 5,709,686 A | 1/1998 | Talos et al. | |
| 5,938,664 A | 8/1999 | Winquist et al. | |
| 6,001,099 A | 12/1999 | Huebner | |
| 6,093,201 A * | 7/2000 | Cooper et al. | 606/232 |
| 6,096,040 A | 8/2000 | Esser | |
| D443,060 S | 5/2001 | Benirschke et al. | |
| 6,228,085 B1 | 5/2001 | Theken et al. | |
| 6,238,969 B1 * | 5/2001 | Figura et al. | 438/254 |
| 6,309,393 B1 | 10/2001 | Tepic et al. | |
| 6,355,042 B2 | 3/2002 | Winquist et al. | |
| D458,684 S | 6/2002 | Bryant et al. | |
| D458,996 S | 6/2002 | Bryant et al. | |
| D463,557 S | 9/2002 | Bryant et al. | |
| D463,558 S | 9/2002 | Bryant et al. | |
| D463,559 S | 9/2002 | Bryant et al. | |
| D464,136 S | 10/2002 | Bryant et al. | |
| D464,731 S | 10/2002 | Bryant et al. | |
| D470,588 S | 2/2003 | Bryant et al. | |
| 6,623,486 B1 * | 9/2003 | Weaver et al. | 606/281 |
| 6,669,701 B2 | 12/2003 | Steiner et al. | |
| 6,709,686 B1 | 3/2004 | Matthew | |
| 6,719,759 B2 | 4/2004 | Wagner et al. | |
| 6,730,091 B1 * | 5/2004 | Pfefferle et al. | 606/70 |
| 6,955,677 B2 | 10/2005 | Dahners | |
| 7,001,388 B2 | 2/2006 | Orbay et al. | |
| 2004/0059334 A1* | 3/2004 | Weaver et al. | 606/69 |
| 2004/0059335 A1 | 3/2004 | Weaver et al. | |

(Continued)

*Primary Examiner* — Matthew Lawson
(74) *Attorney, Agent, or Firm* — Harness, Dickey

(57) ABSTRACT

A bone plate attachable to a bone for internal fixation. The bone plate has an upper surface and an opposite bone-contacting surface and includes a plurality of threaded through-holes for bone fasteners. The bone plate can include through-holes for passing sutures, and also suture-clearance recesses formed on the bone-contacting surface. Each suture-clearance recess is defined proximate to at least one of the suture holes for providing suturing clearance for a suturing instrument, such as a curved suturing needle.

23 Claims, 6 Drawing Sheets

(56) References Cited

U.S. PATENT DOCUMENTS

| | | |
|---|---|---|
| 2004/0102777 A1 | 5/2004 | Huebner |
| 2004/0116930 A1 | 6/2004 | O'Driscoll et al. |
| 2005/0010226 A1* | 1/2005 | Grady et al. ............ 606/69 |
| 2005/0015089 A1 | 1/2005 | Young et al. |
| 2005/0070904 A1 | 3/2005 | Gerlach et al. |
| 2005/0080421 A1* | 4/2005 | Weaver et al. ............ 606/69 |
| 2005/0107796 A1 | 5/2005 | Gerlach et al. |
| 2005/0182405 A1* | 8/2005 | Orbay et al. ............ 606/69 |
| 2005/0182406 A1* | 8/2005 | Orbay et al. ............ 606/69 |
| 2005/0240187 A1* | 10/2005 | Huebner et al. ............ 606/69 |
| 2006/0004361 A1 | 1/2006 | Hayeck et al. |
| 2006/0004362 A1 | 1/2006 | Patterson et al. |
| 2006/0009771 A1* | 1/2006 | Orbay et al. ............ 606/69 |
| 2006/0035772 A1 | 2/2006 | Golesh et al. |
| 2006/0116679 A1 | 6/2006 | Lutz et al. |
| 2006/0173458 A1 | 8/2006 | Forstein et al. |
| 2006/0235400 A1* | 10/2006 | Schneider ............ 606/69 |
| 2006/0264947 A1* | 11/2006 | Orbay et al. ............ 606/69 |
| 2006/0276896 A1* | 12/2006 | Fallin et al. ............ 623/16.11 |
| 2007/0083207 A1* | 4/2007 | Ziolo et al. ............ 606/73 |
| 2007/0088360 A1* | 4/2007 | Orbay et al. ............ 606/69 |
| 2007/0093835 A1* | 4/2007 | Orbay et al. ............ 606/69 |

\* cited by examiner

CONTOURED BONE PLATE

CROSS-REFERENCE TO RELATED APPLICATIONS

This application claims the benefit of U.S. Provisional Application No. 60/791,228, filed on Apr. 11, 2006. The disclosure of the above application is incorporated herein by reference.

INTRODUCTION

There are numerous orthopaedic bone plates for the femur and tibia that have surfaces approximating the corresponding human bone surfaces. One reason for such design is to diminish possible soft tissue irritation by the implanted plate. However, when such plates are implanted with bone anchors, such as screws or other fasteners, irritation of the surrounding soft tissues may still occur, because an otherwise smooth surface becomes interrupted by the heads of the bone anchors, portions of which may protrude in various directions.

Thus there is still a need for procedures and plating assemblies that may further reduce soft tissue irritation.

SUMMARY

The present teachings provide an orthopaedic device that includes a bone plate attachable to a bone. The bone plate has an upper surface and an opposite bone-contacting surface. The bone-contacting surface can be shaped to at least generally conform to a plate-contacting surface of the bone. The upper surface of the bone plate can be generally parallel to the bone-contacting surface so as to define a nominal bone plate thickness. The bone plate can include at least one fastener hole extending between the upper surface and the bone-contacting surface, and a bone fastener having a head that can engage the fastener hole. The upper surface of the bone plate can include at least one modified portion adjacent to the at least one fastener hole. The modified portion can be shaped to increase a thickness of the bone plate beyond the nominal thickness, such that no portion of the head of the bone fastener extends above the upper surface of the bone plate, when the head is disposed in the fastener hole.

The present teachings also provide a bone plate attachable to a bone and having an upper surface and an opposite bone-contacting surface. The bone plate can include threaded fastener holes extending between the upper surface and the bone-contacting surface, and a plurality of suture holes. The bone-contacting surface is shaped to generally conform to a plate-contacting surface of the bone and includes a plurality of suture-clearance formations defined proximate to the suture holes.

In another aspect the present teachings provide a bone plate attachable to a bone. The bone plate has an upper surface and an opposite bone-contacting surface, and can include a plurality of threaded fastener holes and a plurality of suture holes. The bone-contacting surface can include a plurality of suture-clearance recesses defined proximate to the suture holes. The upper surface of the bone plate can include a plurality of modified portions adjacent and surrounding the fastener holes. The modified portions can have a thickness greater than a nominal thickness of the bone plate.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from, but is not limited by, the detailed description and the accompanying drawings, wherein.

DESCRIPTION OF VARIOUS ASPECTS

Figure 1:
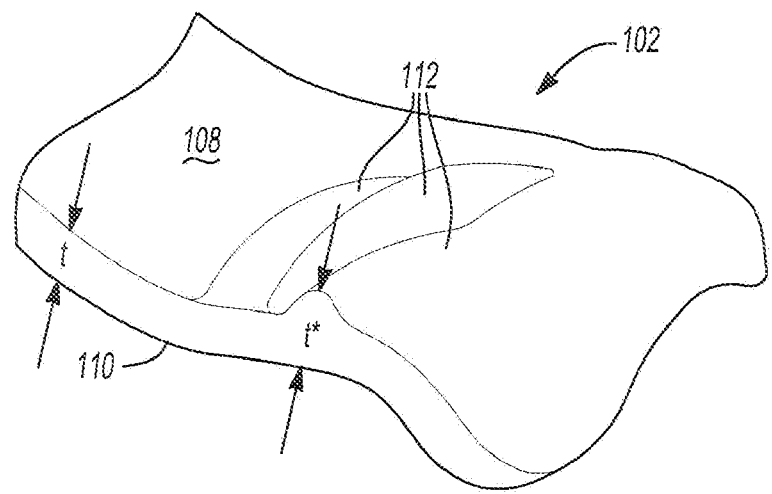
FIG. 1 is a simplified partial perspective view showing only the contour of a bone plate according to the present teachings.
Figure 2:
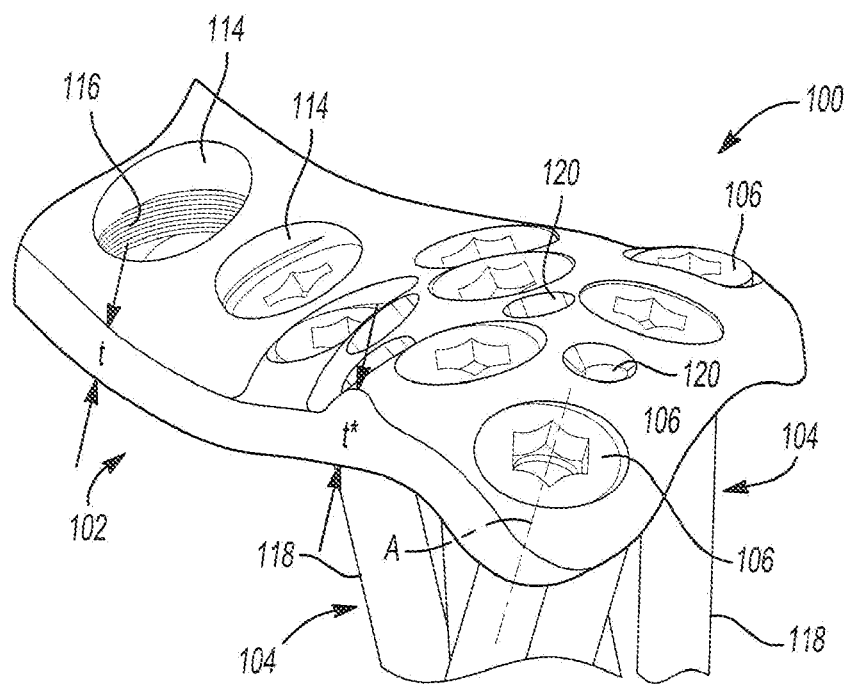
FIG. 2 is a partial perspective view of a plate assembly according to the present teachings.

The following description is merely exemplary in nature and is in no way intended to limit the invention, its applications, or uses. For example, the present teachings can be used for various plating systems, including, but not limited to, systems for the proximal tibia, the distal tibia, the proximal femur, the distal radius, the humerus, and the elbow.

Referring to FIGS. 1-13, exemplary bone plate assemblies 100 according to the present teachings are illustrated. The bone plate assembly 100 can include a bone plate 102 that has a bone-contacting lower surface 110 and an opposite supper surface 108. The bone-contacting surface 110 can be shaped to substantially or generally conform or mate with a corresponding plate-contacting surface of the bone 80. Referring to FIG. 5, the upper surface 108 can be substantially parallel to the lower surface 110 defining a nominal thickness "t", except in selected surface regions 112, in which the upper surface 108 has been modified to define an increased thickness t*, as explained below.

Figure 8:
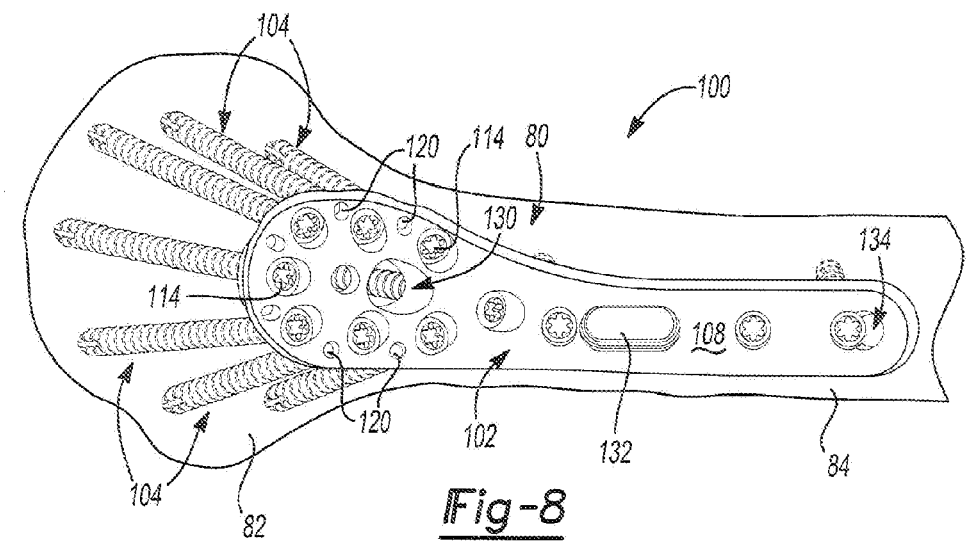
FIG. 8 is an environmental top view of a plate assembly according to the present teachings, shown operatively associated with a bone.
Figure 11:
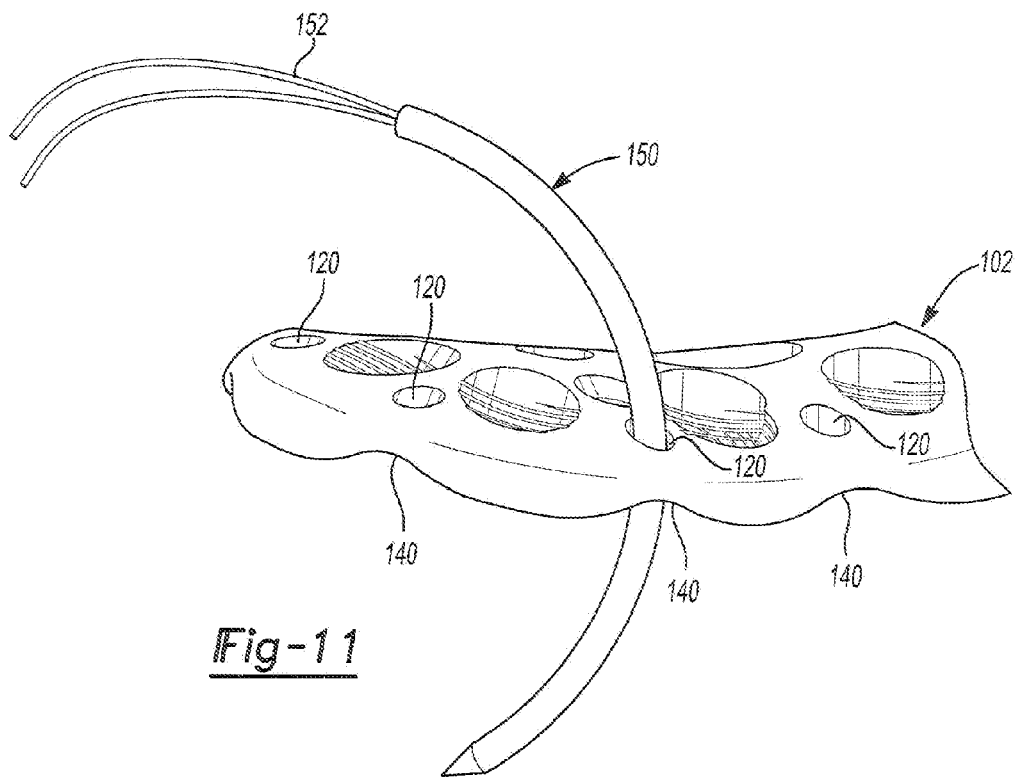
FIGS. 11 and 12 are perspective views of a bone plate shown with a suturing instrument according to the present teachings.
Figure 12:
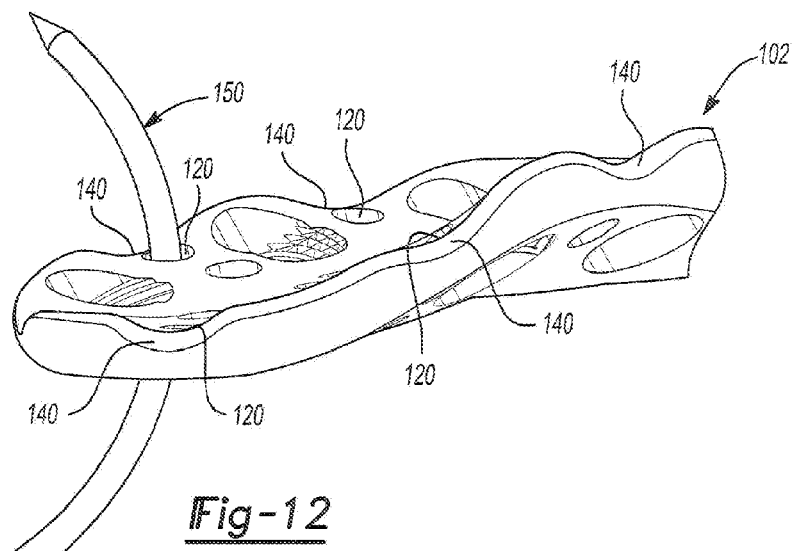
Figure 13:
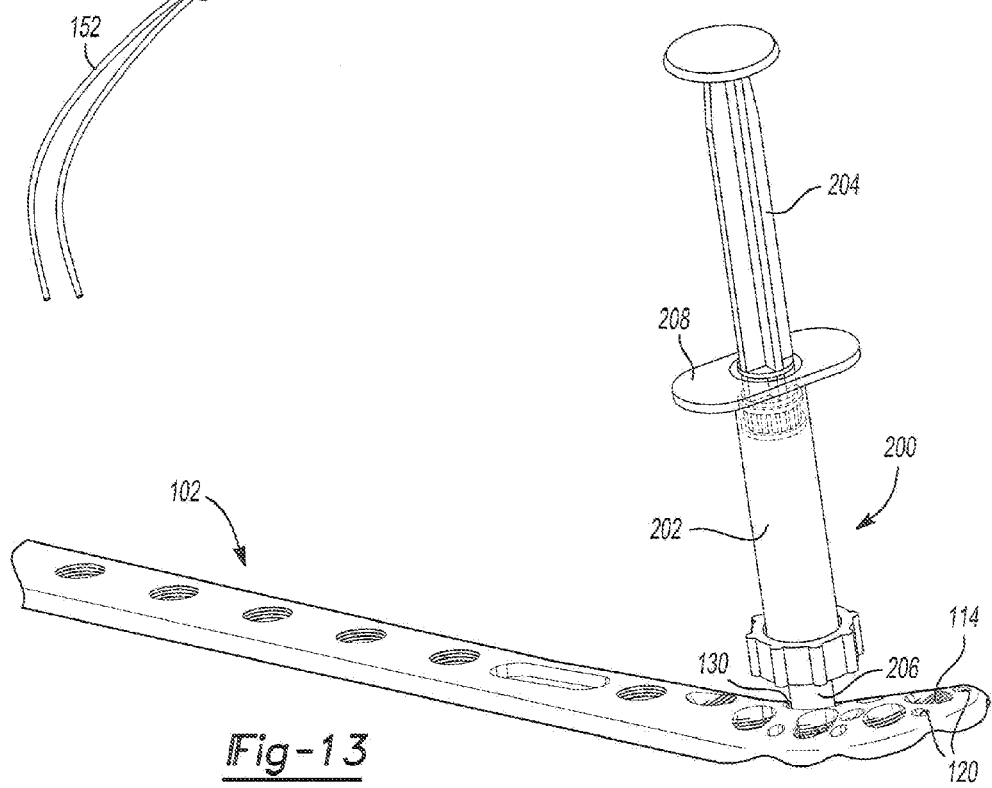
FIG. 13 is a perspective view of a bone plate shown with a graft delivery device according to the present teachings.

The bone plate 102 can include one or more fastener holes 114 for receiving corresponding bone fasteners 104, and one or more suture holes 120 for receiving sutures and/or guide wires. The suture holes 120 can be unthreaded and define smooth inner wall for reducing suture damage. The suture holes 120 can be of a size adequate for passing a suture 152 with a suture instrument 150, as shown in FIGS. 11 and 12. The suture holes 120 can be of smaller diameter than the fastener holes 114. Referring to FIG. 8, the bone plate 102 can also include at least one large non-threaded graft hole 130 for injecting osteobiologics for bone graft applications with a delivery device 200, as shown in FIG. 13. The graft hole 130 can be larger in diameter than the fastener holes 114. The delivery device 200 can be, for example, syringe-like, and can include an outer tube 202 and a plunger 204 slidably received in the tube 202. The outer tube 202 can include a proximal stop flange 208 and a distal tip portion 206. The delivery device 200 can be loaded with the osteobiologic or other graft or pharmacological substance, and the tip portion 206 can be inserted through the graft hole 130. The plunger 204 can be pushed toward the stop flange 208 expelling the substance through the tip portion 206.

Figure 9:
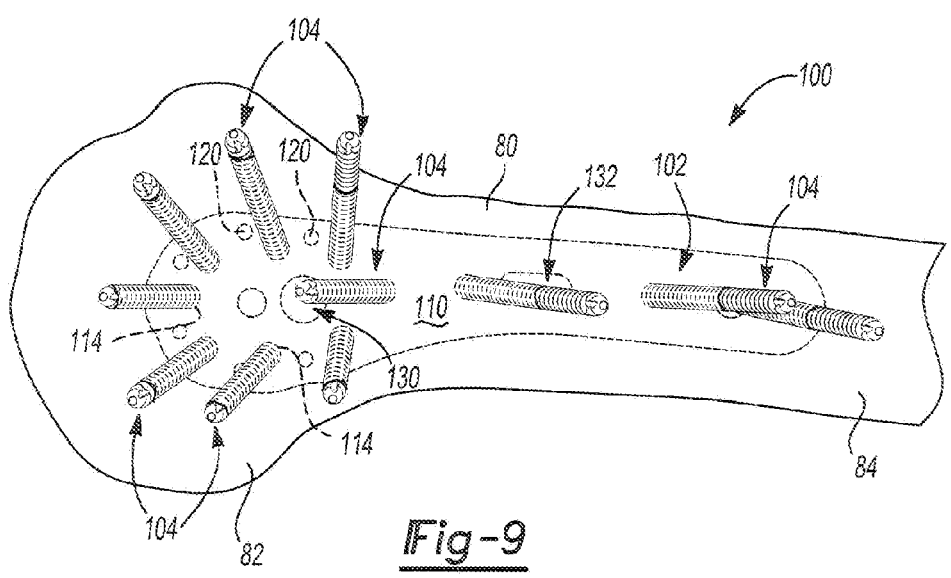
FIG. 9 is an environmental bottom view of the plate assembly of FIG. 8, shown operatively associated with a bone.

The bone plate 102 can also include a fully threaded elongated slot 132, and an opening 134 formed by two communicating threaded holes for providing the surgeon with choice of two different trajectories for the bone fasteners 104, as shown in FIGS 8 and 9. The fastener holes 114 can be threaded and configured so that they can be used with locking or non-locking bone fasteners 104. Each bone fastener 104 can include a head 106 and a bone engaging portion 118. The head 106 can be threaded for locking applications, or unthreaded for non-locking applications. The fastener holes 114 and the heads 106 of the bone fasteners 104 can cooperate by their corresponding threads or other interconnection systems, such as integral or modular interlocking devices including expandable rings, various slotting arrangements, and others, such that the bone fasteners 104 can be locked in a pre-determined orientation, as shown in FIG. 9, or, in other aspects, allowed to angulate. As illustrated in FIG. 4, the threads 116 can be oriented at an angle relative to the upper surface 108 of the plate 102, such that the bone fastener 104 can extend along a predetermined direction A defining a trajectory for the orientation of the head 106 of the bone fastener 104.

Figure 3:
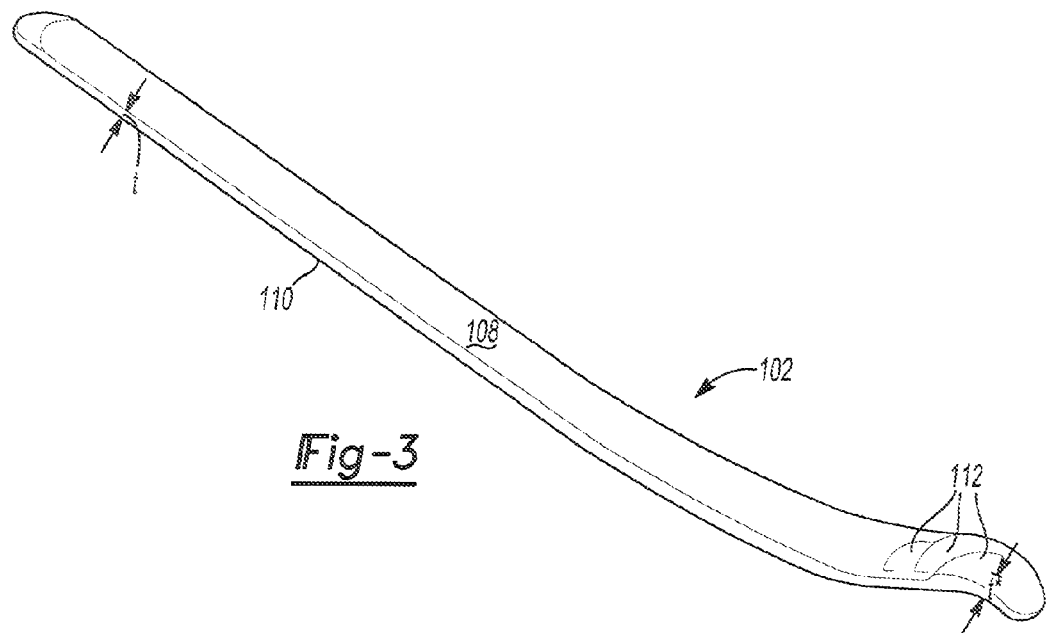
FIG. 3 is a simplified full perspective view of the bone plate shown in FIG. 1.
Figure 4:
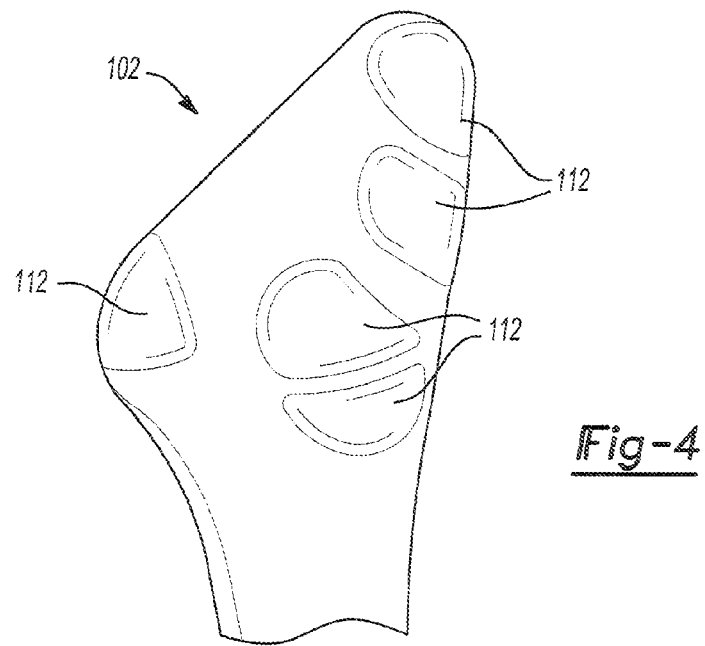
FIG. 4 is a plan view of a portion of the bone plate shown in FIG. 1.
Figure 5:
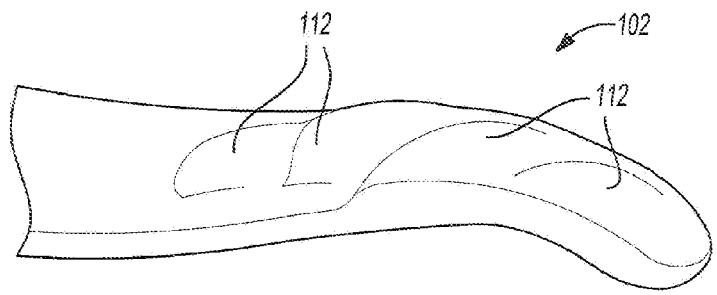
FIG. 5 is a partial side perspective view of the bone plate shown in FIG. 3.
Figure 6:
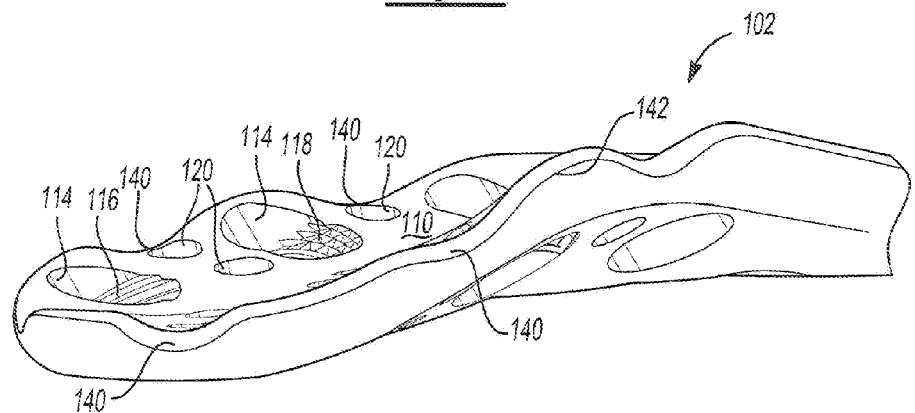
FIG. 6 is a bottom perspective view of a portion of a bone plate according to the present teachings.
Figure 7:
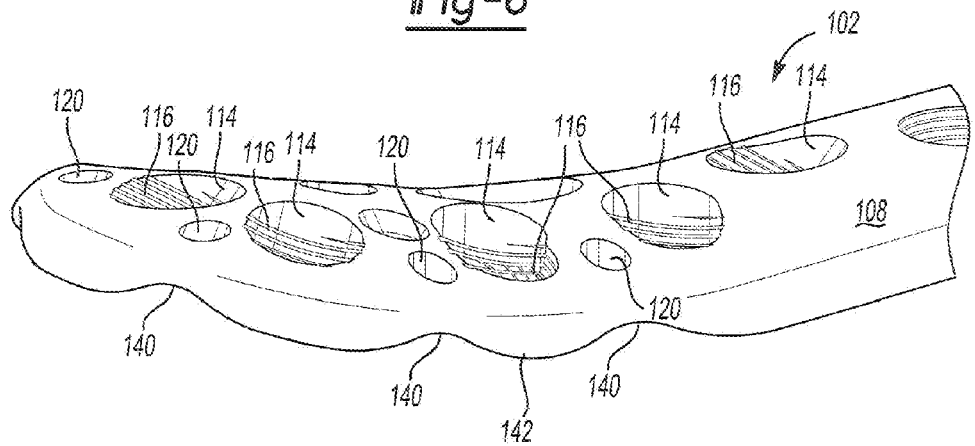
FIG. 7 is a top perspective view of the bone plate of FIG. 6.

Referring to FIGS. 3 and 4, the upper surface 108 of the bone plate 102 can be modified to create the surface regions 112 which are shaped such that when the bone fasteners 104 are inserted through the corresponding fastener holes 114, the heads 106 of the bone fasteners 104 do not protrude above the modified upper surface 108 of the bone plate 102. In other words, the heads 106 of the bone fasteners 104 are flush with, or recessed, with respect to adjacent portions of the upper surface 108. For example, material can be added to the bone plate 102 in a manner that follows the expected trajectory of the head 106 of the fastener 104 throughout a range of orientations, or generally in a manner such that the head 106 remains at or below the upper surface 108 of the bone plate 102 without diminishing the thickness of the bone plate 102 or compromising its strength. It will be appreciated that the upper surface 108 of the bone plate 102 can be modified by various methods, including computer-aided processes that determine the expected trajectories of the heads 106 and determine the modifications required for the profile of the bone plate 102 to avoid protrusion of the heads 106 above the upper surface 108 of the bone plate 102, thereby creating the surface regions 112 which have increased thickness t* relative to the nominal thickness t. It will be appreciated that the bone plate assembly 100 of the present teachings may help reduce or substantially eliminate impingement of the heads 106 of the bone fasteners 104 on the surrounding soft tissues.

Referring to FIGS. 6-12, the bottom surface 110 of the bone plate 102 can define suture-clearance formations 140 placed in relative proximity with corresponding suture holes 120 for facilitating suturing the bone plate 102 through the suture holes 120 and onto muscle tissue associated with the bone 80 in various surgical repair procedures, such as, for example, rotator cuff or other shoulder procedures. The suture-clearance formations 140 can be located and configured for providing easy access to a suturing instrument 150 carrying a suture 152, and allowing clearance for suturing manipulation, as shown in FIGS. 11 and 12. The suture-clearance formations 140 can be in the form of undulations or recesses sized to accommodate passing of the suturing instrument 150, which can be a curved or straight suturing needle, for example. Each suture-clearance formation 140 can extend from a perimeter 142 of bone-contacting surface 110 toward one of the suture holes 120. The shape and placement of the suture-clearance formations 140 in relation to the suture holes 120 can facilitate manipulation of the suturing instrument 150 by the operating surgeon. The suture-clearance formations 140 can define an undulating or wavy shape on the perimeter 142 of the bone-contacting surface 110.

Figure 10:
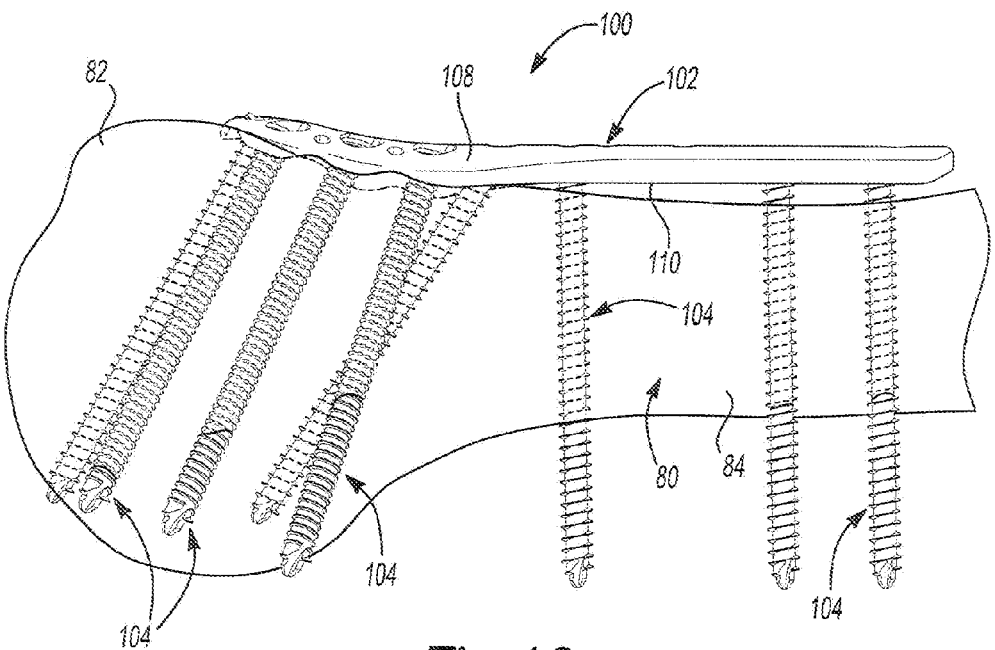
FIG. 10 is an environmental side view of the plate assembly of FIG. 8, shown operatively associated with a bone.

Referring to FIGS. 8-10, the holes 114 can provide threading configured and oriented such that the trajectories of the bone fasteners 104 can follow the shape of the underlying bone portion, such as the humeral head 82, the humeral shaft 84, or other bone portion. The orientation of the bone fasteners associated with the humeral head 82, for example, can be at an angle of 30-45 degrees relative to the orientation of the bone fasteners associated with the shaft 84, as shown in FIG. 10.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention

What is claimed is:

1. An orthopaedic device comprising:
   a bone plate attachable to a bone and including an upper surface and a bone-contacting surface cooperating to define a nominal thickness of said bone plate, said upper surface including a plurality of raised portions having a greater thickness than said nominal thickness and being formed on an opposite side of said bone plate than said bone-contacting surface;
   a plurality of fastener holes extending between said upper surface and said bone-contacting surface and disposed adjacent to said plurality of raised portions, said plurality of fastener holes positioned relative to said plurality of raised portions such that fasteners respectively received within said plurality of fastener holes are flush with or recessed from said upper surface;
   a plurality of suture holes extending between said upper surface and said bone-contacting surface; and
   an undulating perimeter defining a plurality of suture-clearance formations disposed adjacent to said plurality of suture holes, said plurality of suture-clearance formations providing a clearance between said bone-contacting surface of said bone plate and a bone.

2. The orthopaedic device of claim 1, wherein said bone plate includes at least one non-threaded graft hole extending between said upper surface and said bone-contacting surface.

3. The orthopaedic device of claim 1, wherein at least one of said plurality of fastener holes includes threading.

4. The orthopaedic device of claim 3, wherein said threading engages a head of a fastener received within said fastener hole.

5. The orthopaedic device of claim 4, wherein said head of said fastener includes threading that matingly engages said threading of said at least one fastener hole.

6. The orthodaedic device of claim 4, wherein said threading is operable to engage said fastener at a variable angle relative to said bone plate.

7. The orthopaedic device of claim 1, wherein said bone plate includes an elongated slot having threading along its entire perimeter.

8. The orthopaedic device of claim 1, wherein said bone plate includes an opening defined by two adjacent threaded holes communicating with one another.

9. An orthopaedic device comprising:
- a bone plate attachable to a bone and including an upper surface and a bone-contacting surface cooperating to define a nominal thickness of said bone plate, said upper surface including a plurality of raised portions having a greater thickness than said nominal thickness and being formed on an opposite side of said bone plate than said bone-contacting surface;
- a plurality of fastener holes extending between said upper surface and said bone-contacting surface and disposed adjacent to said plurality of raised portions; and
- a plurality of fasteners each including a head positionable relative to said bone plate in a plurality of orientations when respectively received within said plurality of fastener holes, said plurality of raised portions being positioned relative to said plurality of fastener holes such that said head of each of said plurality of fasteners is flush with or recessed from said upper surface in each of said plurality of orientations.

10. The orthopaedic device of claim 9, wherein said bone plate includes at least one non-threaded graft hole extending between said upper surface and said bone-contacting surface.

11. The orthopaedic device of claim 9, wherein each of said plurality of fastener holes includes threading.

12. The orthopaedic device of claim 11, wherein said threading engages said heads of said fasteners received within said fastener holes.

13. The orthopaedic device of claim 12, wherein said heads of said fasteners include threading that matingly engages said threading of said fastener holes.

14. The orthopaedic device of claim 9, wherein said bone plate includes an elongated slot having threading along its entire perimeter.

15. The orthopaedic device of claim 9, wherein said bone plate includes an opening defined by two adjacent threaded holes communicating with one another.

16. An orthopaedic device comprising:
- a bone plate attachable to a bone and including an upper surface and a bone-contacting surface;
- a plurality of fastener holes extending between said upper surface and said bone-contacting surface;
- a plurality of suture holes extending between said upper surface and said bone-contacting surface; and
- a perimeter disposed about said bone-contacting surface defining an undulating shape on at least a portion thereof, said undulating shape including a series of alternating convex regions and concave regions extending a distance away from said bone-contacting surface and defining a plurality of suture-clearance formations disposed adjacent to said plurality of suture holes, said concave regions extending between a pair of said convex regions and toward a respective one of said plurality of suture holes to provide a clearance between said bone-contacting surface of said bone plate and a bone.

17. The orthopaedic device of claim 16, wherein said bone plate includes at least one non-threaded graft hole extending between said upper surface and said bone-contacting surface.

18. The orthopaedic device of claim 16, wherein at least one of said plurality of fastener holes includes threading.

19. The orthopaedic device of claim 18, wherein said threading engages a head of a fastener received within said fastener hole.

20. The orthopaedic device of claim 19, wherein said head of said fastener includes threading that matingly engages said threading of said fastener hole.

21. The orthodaedic device of claim 19, wherein said threading is operable to engage said fastener at a variable angle relative to said bone plate.

22. The orthopaedic device of claim 16, wherein said bone plate includes an elongated slot having threading along its entire perimeter.

23. The orthopaedic device of claim 16, wherein said bone plate includes an opening defined by two adjacent threaded holes communicating with one another.

* * * * *